United States Patent [19]

Karsai et al.

[11] Patent Number: 4,844,726
[45] Date of Patent: Jul. 4, 1989

[54] HERBICIDAL COMPOSITIONS WITH PROLONGED ACTION AND IMPROVED SELECTIVITY

[75] Inventors: József Karsai, Velence; Endre Sebestyen, Agárd; József Palik, Budapest; István Karsai, Battonya; György Kis, Budapest; Rózsavölgyi, Velence; Imre Varga; Traján Kreszta, both of Battonya; János Czibor, Budapest, all of Hungary

[73] Assignee: Nitrokemia Ipartelepek, Fuzfogyartelep, Hungary

[21] Appl. No.: 824,710

[22] PCT Filed: Apr. 19, 1985

[86] PCT No.: PCT/HU85/00026

§ 371 Date: Feb. 7, 1986

§ 102(e) Date: Feb. 7, 1986

[87] PCT Pub. No.: WO85/04783

PCT Pub. Date: Nov. 7, 1985

[30] Foreign Application Priority Data

Apr. 20, 1984 [HU] Hungary ............................ 1540/84
Dec. 20, 1984 [HU] Hungary ............................ 1540/84
Apr. 17, 1985 [HU] Hungary ............................ 1540/84

[51] Int. Cl.⁴ ............................................. A01N 05/22
[52] U.S. Cl. ............................................. 71/87; 71/100; 71/118
[58] Field of Search ........................... 71/87, 118, 100

[56] References Cited

U.S. PATENT DOCUMENTS

| | | | |
|---|---|---|---|
| 2,494,283 | 1/1950 | Cassaday et al. | 260/461 |
| 3,176,035 | 3/1965 | Lutz et al. | 260/461 |
| 3,845,171 | 10/1974 | Beriger | 260/943 |
| 3,888,979 | 6/1975 | Beriger | 424/211 |
| 3,920,771 | 11/1975 | Beriger | 260/943 |
| 3,933,945 | 1/1976 | Beriger | 260/943 |
| 4,648,894 | 3/1987 | Gray et al. | 71/87 |
| 4,652,298 | 3/1987 | Gray et al. | 71/87 |
| 4,662,930 | 5/1987 | Gray et al. | 71/87 |

*Primary Examiner*—Catherine L. Mills
*Attorney, Agent, or Firm*—Herbert Dubno; Jonathan Myers

[57] ABSTRACT

The invention relates to a composition for the extension and increase of the activity of herbicidal compositions containing as herbicidally active ingredient at least one carbamate and/or thiolcarbamate and/or chloroacetanilide and/or dichloroacetanilide derivative and optionally antidotes therefore, which comprises at least one thio- or dithiophosphoric acid ester of the formula (I)

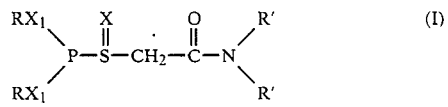

wherein

R stands for identical or different alkyl, alkenyl, isoalkyl, isoalkenyl, haloalkyl, haloalkenyl, isohaloalkyl or isohaloalkenyl groups, each containing up to 4 carbon atoms;

R' represents identical or different alkyl, alkenyl, isoalkyl, isoalkenyl, haloalkyl, haloalkenyl, isohaloalkyl, isohaloalkenyl groups, each containing up to 4 carbon atoms;

X is oxygen or sulfur, $X_1$ is oxygen or sulfur, with the proviso that at least one of the $X_1$ groups is other than oxygen.

3 Claims, No Drawings

HERBICIDAL COMPOSITIONS WITH PROLONGED ACTION AND IMPROVED SELECTIVITY

The invention relates to novel herbicidal compositions and to a process for employing these compositions. More particularly, the invention concerns novel herbicidal compositions comprising thio- or dithiophosphoric acid esters in association with herbicides of the carbamate, thiolcarbamate, chloroacetanilide or dichloroacetanilide type or any desired combination of two or more of such herbicidally active ingredients and optionally antidotes. The invention further provides a process for the application of these compositions or compositions containing the active ingredients separately.

The thio- or dithiophosphoric acid esters employed in the compositions according to the invention are encompassed by the following formula (I)

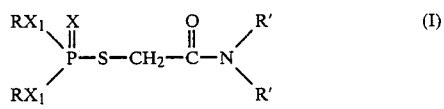

in which
R stands for identical or different alkyl, alkenyl, isoalkyl, isoalkenyl, haloalkyl, haloalkenyl, isohaloalkyl or isohaloalkenyl groups each having up to 4 carbon atoms in the alkyl and alkenyl moieties, respectively;
R' represents identical or different alkyl, alkenyl, isoalkyl, isoalkenyl, haloalkyl, haloalkenyl, isohaloalkyl or isohaloalkenyl groups each having up to 4 carbon atoms in the alkyl and alkenyl moieties, respectively;
X is oxygen or sulfur;
$X_1$ is oxygen or sulfur
with the proviso that at least one of the $X_1$ substituents is other than oxygen.

Compounds of the formula (I), wherein the substituents are as hereinabove defined, can be prepared in a known manner, for example following the reaction illustrated on Chart A.

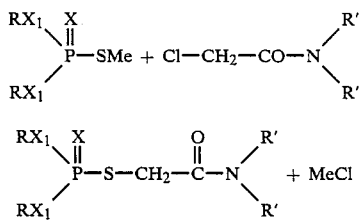

The process is generally carried out under atmospheric pressure, at a temperature between 0° C. and 80° C., in a medium inert under the reaction conditions. The starting compounds are known in the art or can be prepared in a known manner.

The insecticidal activity of the compounds of formula (I) is known in the art. It has, however, not been disclosed in the prior art that these compounds increase and extend the activity of carbamate, thiolcarbamate, chloroacetanilide and dichloroacetanilide herbicides. Another newly discovered property of the compounds of formula (I) is that they increase and extend the activity of antidotes conventionally used in combination with thiolcarbamate and chloroacetanilide herbicides.

The increase in activity and its duration is achieved without any harmful side-effect on the cultivated plants.

BACKGROUND ART

Herbicides of the carbamate, thiolcarbamate, chloroacetanilide and dichloroacetanilide type are widely used in the everyday practice of agriculture. They are for example disclosed in the U.S. Pat. Nos. 2,863,752; 2,864,683; 3,442,945; 2,913,327; 2,695,225; 2,906,614; 3,330,643; 3,330,821; 3,330,642; 3,198,786; 3,573,031 and 3,175,897.

As previously stated, herbicides are widely used in agriculture. The herbicidally active chloroacetanilide and thiolcarbamate derivatives, however, injure the cultivated plants as well, they are therefore often combined with various antidotes. Certain antidotes, which reduce the phytotoxic effect of thiolcarbamate herbicides on agricultural plants show a protecting effect in combination with chloroacetanilide herbicides, too, in various cultures, e.g. maize [J. Robert, C. Levitt, D. Penner: J. Agr. Food. Chem. 27(3), 533–536 (1979)]. Such antidotes are for example disclosed in the Belgian Patent Specifications Nos. 782,120 and 806,038, in the U.S. Pat. Nos. 3,893,838 and 3,931,313 and in the Hungarian Patent Specifications Nos. 165,736, 176,784 and 168,977.

In addition to their toxic effect on the cultivated plants, another problem in connection with these herbicidally active ingredients is that the duration of their effect is not satisfactory.

As it is well known, immediately after spraying the concentration of the above-mentioned herbicides and antidotes is very high in the upper layer of the soil, but later on it decreases rapidly. This may lead to an invasion of weeds and, as a result, to the injury of cultivated plants. The reasons for this phenomena are discussed by Kaufman, D. D.-Kearney, P. C. (Appl. Microbiol. 13, 443–446 (1965)) and Fox, J. L. (Science, 225, 1029–1031 (1983)). It is concluded that especially the active ingredients containing mn—C=(O) groups are rapidly decomposed by the microbes present in the soil.

DETAILED DESCRIPTION OF THE INVENTION

In our experiments carried out with the aim of extending the duration of the effect of carbamate, thiolcarbamate, chloroacetanilide and dichloroacetanilide herbicides, optionally combined with antidotes we have surprisingly found that the thio- and dithiophosphoric acid ester derivatives according to the invention prolong the action of said herbicides, increase their activity and improve their selectivity. In addition, we have found, that the action of the simultaneously used antidotes is also extended and their activity is increased.

By using the thio- and dithiophosphoric acid ester derivatives according to the invention the duration of herbicidal effect can be optimalized, the doses of the herbicides employed can be reduced, their selectivity can be increased, and similar favorable effects can be achieved also when the compounds according to the invention are employed in association with antidotes.

By employing the extenders according to the invention, the herbicidal compositions comprising carbamates, thiolcarbamates, chloroacetanilides and/or dichloroacetanilides as herbicidally active ingredient and optionally antidotes can be used more advantageously in maize, sunflower, cereals, soya, sugar beet, vegetables and fruits than the hitherto employed compositions containing the above-mentioned active ingredients and optionally antidotes.

The extenders according to the invention are particularly effective in combination with S-ethyl bis-(2-methylpropyl)-carbamothioate, S-ethyl cyclohyxythyl-carbamothioate, S-(2,3-dichloroallyl)-diisopropylthiocarbamate, S-ethyl dipropylcarbamothioate, S-ethyl-N,N-hexamethylene-thiocarbamate, S-propyl-dipropyl-thiocarbamate, 2-chloroallyl-diethyl-dithioarbamate, 1-methylethyl-3-chlorophenylcarbamate, 4-chloro-2-butinyl-3-chlorophenyl-carbamate, 2-chloro-2,6-diethyl-N-methoxymethyl-acetanilide, 2-chloro-2-methyl-6-ethyl-N-methoxyethyl-acetanilide, N-butoxymethyl-2-chloro-2,6-diethyl-acetanilide, N-chloroacetyl-N-(2,6-diethylphenyl)-glycine, 2-chloro-N-(1,6-dimethyl-phenyl)-N-(methoxyethyl)-acetamide, N-(2-chloroethyl)-2,6-dinitro-N-propyl-4-(trifluoromethyl)-aniline, 2-chloro-N-(2,6-dimethylphenyl)-N-(1H-pyrazik-1-yl-methyl)-acetamide, 2-chloro-N-(2-ethyl,6-methyl-phenyl)N-(2-methoxy-1-methylethyl)-acetamide, 2-chloro-N-(2,6-diethylphenyl)-N-(2-propoxyethyl)-acetamide, 2-chloro-N-(1methylethyl)-N-phenyl-acetamide and N,N-diallylchloroacetanilide, and optionally antidotes.

The compositions containing the compounds of formula (I) as extenders in combinations with the above-mentioned herbicides and optionally antidotes can be applied to the soil or the plants or incorporated into the soil prior to or after sowing, pre- or postemergently, depending on the properties of the herbicides present in the compositions. Alternatively, the herbicides, antidotes and the compounds according to the invention may be formulated separately and can be employed simultaneously or subsequently, but the time interval between the application of the individual components should be minimalized.

The dose of the compounds according to the invention and the mutual proportions of the various components may be varied within a wide range. The actual dose is a function of the chemical and physical properties of the herbicides, the cultivated plants, weeds, type of the soil, climatic factors and further similar conditions which are well known for those skilled in the art.

In the combinations according to the invention the ratio of the herbicidally active component to the thio- or dithiophosphoric acid esters of the formula (I) generally is between 30:1 and 1:1, preferably 10:1 and 3:1, most preferably 6:1 and 5:1.

The quantity of the thio- or dithiophosphoric acid ester component in the first line depends on the microbial activity of the soil. Generally it is employed in an amount of 0.1 to 8.0 kg, preferably 0.2 to 3.0 kg, most preferably 0.5 to 3.0 kg per hectare.

In the combinations according to the invention the antidotes are generally used in the usual ratios related to the herbicides, but lower doses are also possible.

The total active ingredient concentration in the compositions according to the invention is 0.1 to 95% by mass, preferably 1 to 90% by mass.

From the concentrated compositions according to the invention the ready-to-use formulations are prepared by dilution. The formulation prepared by the admixture of the herbicides, the extenders according to the invention and optionally the antidotes directly prior to application (e.g. tank mixtures) which are, if desired, diluted, are also within the scope of the invention. The compositions containing the extender alone generally contain 0.1 to 95% by mass, preferably 1 to 90% by mass of active ingredient.

The compositions according to the invention may be formulated as solid or liquid preparations conventionally used in the agriculture, depending on the physical and chemical properties of the active ingredient(s). The compositions contain the active ingredient(s) in association with acceptable, non-phytotoxic solid or liquid carriers and optionally surfactants.

The compositions optionally contain further additives, which have a favorable influence on the activity, e.g. decrease the volatility of the active ingredients or facilitate the application. Such additives include protecting colloids, thickening agents, adhesives, stabilizers and solid carriers with high adsorption capacity.

The compositions according to the invention generally contain in addition to the above-defined amount of active active ingredient(s) 1 to 99% by mass of solid or liquid carriers and optionally surfactants.

As a carrier any non-phytotoxic inorganic or organic material of natural or synthetic origin may be employed. Solid carriers include clays, natural or synthetic silicates, silicic acid, dolomite, kaoline, diatomaceous earth, flour of vegetable products, starch, etc. As a liquid carrier for example water, alcohols, esters, ketones, mineral oil fractions, aromatic, aliphatic or cyclic hydrocarbons, halogenated hydrocarbons, dimethyl sulfoxide, etc. can be employed.

The surface active agents include emulsifying, dispersing and wetting agents, which are of ionic and/or non-ionic character. Typical representatives of surfactants are the salts of ligninesulfonic acid, salts of phenol- and naphthalinesulfonic acids, polycondensation product of ethylene oxide with fatty alcohols or fatty acids or fatty acid amides, arlalkylsulfonates, substituted phenols, e.g. alkyl- and arylphenols.

The solid compositions according to the invention may be finished as powders, dusting powders, granulates, etc., while the liquid formulations include solutions, emulsifiable concentrates, emulsions, concentrated suspensions, wettable powders, sprays or pastes. The concentrated formulations may be diluted as desired, and are prepared in a conventional manner.

The compositions according to the invention may be employed simultaneously with other plant protecting agents, e.g. herbicides, pesticides, fungicides, bactericides, and plant growth regulators. Generally any plant protecting agent which is compatible with the chloroacetanilide, dichloroacetanilide, carbamate and thiolcarbamate herbicides is suitable for simultaneous application.

According to the invention the formulations containing an effective amount of one or more herbicides of the carbamate, thiolcarbamate, chloroacetanilide and dichloroacetanilide type and optionally antidotes in association with the thio- and dithiophosphoric acid esters of the formula (I) are applied to the plants or the soil containing the seeds of the plants. Alternatively, the herbicidally active ingredients and/or the antidotes and/or the extenders according to the invention may be formulated separately, and applied to the plants or to the soil either simultaneously or subsequently. The active ingredients are employed in an effective amount.

The formulations are applied to the plants or the soil for example by spraying, dusting, vaporization, etc., using conventional techniques.

The invention is elucidated in more detail by the aid of the following non-limiting Examples.

EXAMPLE 1

O-ethyl-S-n-propyl-S-(di-2-propenylamino)-dithiophosphoric acid ester 30 g of chloroacetic acid-N-(2-propenyl)-amide in 200 ml of acetonitrile are stirred with 40 g of O-ethyl-S-n-propyl-thiophosphoric acid potassium salt at room temperature for 12 hours. After stirring, the reaction mixture is refluxed for 3 hours. The salts precipitated upon cooling are eliminated from the solution, and the solvent is distilled off under reduced pressure. The residue is taken up in 100 ml of methylene chloride and washed with 30 ml of 1 n sodium hydroxide and subsequently 30 ml of water. The solvent is then distilled off on a bath of 40° to 50° C. to yield the title compound with a good yield.

$n_D^{23} = 1.5221$

EXAMPLE 2

O,S-di-2-chloroethyl-S-(di-2-propenylamino)-dithiophosphoric acid ester

Into a flask equipped with a stirrer, thermometer and dropping funnel there are added 25.5 g (0.1 mole) of O,S-di-2-chloroethyl-dithiophosphoric acid, 17.3 g of diallyl-chloroacetamide and 100 ml of benzene. To the mixture 11 g of triethyl amine are slowly added, under vigorous stirring. A rapid reaction takes place, which results in the precipitation of the amine hydrochloride formed. When the addition is complete, the mixture is refluxed for 3 to 4 hours. The hydrochloride formed in the theoretical amount is eliminated by filtration. The filtrate is washed with 50 ml of a 20% sodium hydroxide solution and subsequently with water. The solvent is distilled off in vacuum, and the title compound is obtained with a good yield.

$n_D^{25} = 1.5440$

EXAMPLE 3

O,S-diethyl-S-(di-2-propenylamino)-dithiophosphoric acid ester 18.4 g of O,S-diethyl-dithiophosphoric acid are dissolved in 50 ml of water, and the solution is neutralized with 6.8 g of potassium carbonate. In a flask equipped with a stirrer, thermometer and dropping funnel 17.3 g of diallyl chloroacetamide in 50 ml of acetone are added to the above solution dropwise, at 20° C.

When the addition is complete, the mixture is stirred at 45° to 50° C. for 4 to 5 hours, whereupon it is poured into 500 ml of water and the precipitated oily product is separated. The aqueous phase is extracted with benzene twice, dried over sodium sulfate, and the solvent is distilled off. The title compound is obtained with a good yield.

$n_D^{25} = 1.5205$

The following compounds are prepared in an analogous manner.

| No. | Substituents R | R | R' | R' | $n_D^{25}$ |
|---|---|---|---|---|---|
| 1 | methyl | methyl | propenyl | propenyl | 1.4338 |
| 2 | n-propyl | n-propyl | propenyl | propenyl | 1.5242 |
| 3 | propenyl | propenyl | propenyl | propenyl | 1.5398 |
| 4 | 2-chloro-ethyl | 2-chloro-ethyl | 4-propyl | 4-propyl | 1.5282 |
| 5 | ethyl | 3-chloro-propyl | propenyl | propenyl | 1.5065 |
| 6 | ethyl | i-propyl | propenyl | propenyl | 1.5137 |
| 7 | ethyl | ethyl | 2-chloro-ethyl | 2-chloro-ethyl | 1.5886 |
| 8 | 2-chloro-ethyl | 2-chloro-ethyl | ethyl | n-propyl | 1.5183 |
| 9 | 2-chloro-ethyl | 2-chloro-ethyl | n-propyl | i-butyl | 1.5344 |
| 10 | 2-chloro-ethyl | 3-chloro-propyl | propenyl | propenyl | 1.5013 |

EXAMPLE 4

In the biological tests the active substances according to Examples 1, 2 and 3 and the compound No. 10 were used in the following manner:

40 parts by weight of active ingredient are dissolved in a mixture of 32 parts by weight of xylene and 22 parts by weight of dichloromethane, and to the solution an emulsifying agent containing the mixture of 6 parts by weight of alkylarylsulfonic acid calcium and fatty acid-polyglycol ester is added. The solution is homogenized by stirring and is then filtered. An emulsion concentrate containing 40% by weight of active ingredient is obtained.

EXAMPLE 5

Examination of the duration of activity and increase in herbicidal effect of chloroacetanilide herbicides when combined with the compounds of formula (I)

Test were carried out under foil preemergently, in pots of 12 cm diameter, on "chernosiom" brown forest soil containing 1.63% of humus.

The following treatments were performed:
(1) control
(2) 2-chloro2',6'-diethyl-N-(methoxymethyl)-acetanilide 1 kg/ha (Lasso)
(3) 2-chloro-2',6'-diethyl-N-(methoxymethyl)-acetanilide 2 kg/ha (Lasso)
(4) O,S-diethyl-S-(di-2-propenylamino)-dithiophosphoric acid ester (product according to Example 3) 200 g/ha
(5) O,S-diethyl-S-(di-2-propenylamino)-dithiophosphoric acid ester (product according to Example 3) 500 g/ha
(6) 2-chloro-2',6'-diethyl-N-(methoxymethyl)-acetanilide 1 kg/ha (Lasso)+O,S-diethyl-S-(di-2-propenylamino)-dithiophosphoric acid ester (product according to Example 3) 500 g/ha
(7) 2-chloro-2',6'-diethyl-N-(methoxymethyl)-acetanilide 2 kg/ha (Lasso)+O,S-diethyl-S-(di-2-propenylamino)-dithiophosphoric acid ester (product according to Example 3) 200 g/ha The compositions were used as a tank mixture and applied to the pots in an amount of 220 lit/ha by spraying. As a test plant maize was used. Into each pot 5 seeds were sown. As a weed wild millet (Panicum ssp) was employed, since of the monocotyledonous weeds grown from seeds wild millet is the most resistent to herbicides. Therefore, this test weed is excellently suitable for evaluation of the efficiency of a herbicidal agent or combination. Of wild millet 20 seeds were sown into each pot.

After spraying, the pots containing the cultivated plants and weeds, respectively were kept at 23 to 30° C., the soil was calibrated to a water capacity of 70 to 80% in order to increase the decomposition rate of herbicides. 15 and 30 days after sowing and spraying, the overground vegetable parts were removed and new seeds were sown without substantial admixture of the surface. In this way the activity increasing and herbicide action extending properties of the compounds according to the invention were tested under "provocative" conditions.

Evaluation was carried out on the 15th day. In the case of wild millet the killing ratio (%), in the case of maize the phytotoxicity (EWRC scale) were calculated. On the EWRC scale the score 1 means that there is no phytotoxicity, while the score 9 represents total weed killing. Tests were carried out in four repetitions.

| Effect of the active ingredients on the killing ratio of wild millet (Panicium spp) | | | |
|---|---|---|---|
| No. of treatment according to Example 5 | Killing in % of the control on the | | |
| | 15th | 30th day | 45th |
| 1 | 0 | 0 | 0 |
| 2 | 0 | 0 | 0 |
| 3 | 13 | 0 | 0 |
| 4 | 0 | 0 | 0 |
| 5 | 0 | 0 | 0 |
| 6 | 100 | 100 | 67 |
| 7 | 100 | 100 | 100 |

| The effect of active ingredients on the injury of maize (Zea mays) | | | |
|---|---|---|---|
| No. of treatment according to Example 5 | Phytotoxicity (EWRC-scale) on the | | |
| | 15th | 30th day | 45th |
| 1 | 1 | 1 | 1 |
| 2 | 1 | 1 | 1 |
| 3 | 1 | 1 | 1 |
| 4 | 1 | 1 | 1 |
| 5 | 1 | 1 | 1 |
| 6 | 1 | 1 | 1 |
| 7 | 1 | 1 | 1 |

The test results show that when employed alone both 2-chloro-2',6'-N-(methoxymethyl)-acetanilide and the product according to Example 3 (representing the compounds according to the invention) are ineffective against wild millet. But their efficiency has surprisingly been increased, when the two compositions were employed together. While a 2 kg/ha dose of 2-chloro-2',6'-diethyl-N-(methoxymethyl)-acetanilide showed a slight effect against wild millet on the 15th day only, the test combinations resulted in a 67 to 100% killing of wild millete even according to the evaluation performed on th 45th day. The increase of herbicidal activity had no injurious effect on maize. Accordingly, it can be established that the compounds according to the invention when employed alone in the given doses could not control the most resistant monocotyledonous weed, wild millet. Their combinations with chloroacetanilide herbicides (which are ineffective or have only a slight effect alone), however, are capable of an effective control of wild millet and show an increased duration of activity, i.e. a clear synergism is observed.

EXAMPLE 5a

Examination of the extension of activity, the extent of the reduction of dose, the possibility of combination of antidotes in case of combinations of chloroacetanilide herbicides with the compounds of formula (I)

The test conditions were identical with those described in Example 5. The following treatments were carried out:
(1) control
(2) alachlor (2-chloro-2',6'-diethyl-N-methoxymethyl-acetanilide) 2.0 kg/ha
(3) alachlor 1.0 kg/ha
(4) acetochlor (2-chloro-2'-methyl-6'-ethyl-N-methoxyethyl-acetanilide) 2.0 kg/ha
(5) acetochlor 1.0 kg/ha
(6) butachlor (N-butoxymethyl-2-chloro-2',6'-diethyl-acetanilide) 4.0 kg/ha
(7) butachlor 2.0 kg/ha
(8) diethatyl (N-chloroacetyl-N-(2,6-diethylphenyl)-glycine 4.0 kg/ha
(9) diethatyl 2.0 kg/ha
(10) dimethachlor (2-chloro-N-(2,6-dimethylphenyl)-N-(2-methoxyethyl)-acetamide 2.0 kg/ha
(11) dimethachlor 1.0 kg/ha
(12) pretylachlor (2-chloro-2',6'-diethyl-N-(2-propoxyethyl)-acetanilide 3.0 kg/ha
(13) pretylachlor 1.5 kg/ha
(14) propachlor (2-chloro-N-isopropylacetanilide) 6.0 kg/ha
(15) propachlor 3.0 kg/ha
(16) methazachlor (2-chloro-N-(2,6-dimethylphenyl)-N-(1H-pyrazol-1-ylmethyl)-acetamide 3.0 kg/ha
(17) methazachlor 1.5 kg/ha
(18) metholachlor (2-chloro-N-(2-ethyl-6-methylphenyl)-N-(2-methoxy-1-methylethyl)-acetamide) 2.0 kg/ha
(19) metholachlor 1.0 kg/ha
(20) alachlor 1.0 kg/ha+the product according to Example 2 500 g/ha
(21) acetochlor 1.0 kg/ha+the product according to Example 2 500 g/ha
(22) butachlor 2.0 kg/ha+the product according to Example 2 500 g/ha
(23) diethatyl 2.0 kg/ha+the product according to Example 2 500 g/ha
(24) dimethachlor 1.0 kg/ha+the product according to Example 2 500 g/ha
(25) pretylachlor 1.5 kg/ha+the product according to Example 2 500 g/ha
(26) propachlor 3.0 kg/ha+the product according to Example 2 500 g/ha
(27) methazachlor 1.5 kg/ha+the product according to Example 2 500 g/ha
(28) metholachlor 1.0 kg/ha+the product according to Example 2 500 g/ha
(29) The product according to Example 2 500 g/ha The doses are expressed in the amount of active ingredient.

| Effect of the active ingredients on the killing ratio of wild millet (Panicum spp) | | | |
|---|---|---|---|
| No. of treatments according to Example (5a) | Killing in % of the control on the | | |
| | 15th | 30th day | 45th |
| 1 | 0 | 0 | 0 |
| 2 | 15 | 0 | 0 |
| 3 | 0 | 0 | 0 |
| 4 | 26 | 0 | 0 |
| 5 | 0 | 0 | 0 |
| 6 | 0 | 0 | 0 |

-continued

Effect of the active ingredients on the killing ratio of wild millet (Panicum spp)

| No. of treatments according to Example (5a) | Killing in % of the control on the | | |
|---|---|---|---|
| | 15th | 30th day | 45th |
| 7 | 0 | 0 | 0 |
| 8 | 0 | 0 | 0 |
| 9 | 0 | 0 | 0 |
| 10 | 37 | 0 | 0 |
| 11 | 6 | 0 | 0 |
| 12 | 16 | 0 | 0 |
| 13 | 0 | 0 | 0 |
| 14 | 0 | 0 | 0 |
| 15 | 0 | 0 | 0 |
| 16 | 0 | 0 | 0 |
| 17 | 0 | 0 | 0 |
| 18 | 17 | 0 | 0 |
| 19 | 0 | 0 | 0 |
| 20 | 100 | 84 | 52 |
| 21 | 100 | 100 | 81 |
| 22 | 100 | 17 | 40 |
| 23 | 100 | 63 | 39 |
| 24 | 100 | 100 | 86 |
| 25 | 100 | 86 | 77 |
| 26 | 100 | 100 | 88 |
| 27 | 100 | 92 | 71 |
| 28 | 100 | 88 | 73 |
| 29 | 0 | 0 | 0 |

The results set forth in the Table show that the test herbicides were practically ineffective against wild millet (Panicum ssp.) when employed in the test doses alone. By combining the test herbicides with the compound according to Example 2 of the instant invention their efficiency could considerably be improved. According to the evaluations carried out on the 15th day the herbicidal effect was 100% in case of each combination, while even the results observed on the 45th day show that in spite of the lower doses employed, the activity was increased to an unexpected extent, which could not be foreseen on the basis of the individual activities of the components combined.

EXAMPLE 5b

The biological activity of acetochlor was examined alone and in combination with the product according to Example 3 in maize. The test conditions were identical with those described in Example 5. The following treatments were carried out:
(1) control
(2) acetochlor 2.0 kg/ha
(3) compound according to Example 3 400 g/ha
(4) acetochlor 2.0 kg/ha+compound according to Example 3 400 g/ha
(5) acetochlor 2.0 kg/ha+compound according to Example 3 400 g/ha+N-dichloroacetyl-1-oxy-4-azaspiro-4,5-decane 200 g/ha
(6) acetochlor 2.0 kg/ha+N-dichloroacetyl-1-oxy-4-azaspirodecane 200 g/ha The doses are expressed in the amount of active ingredient.

During evaluation the height of maize was measured to determine whether the compound according to Example 3 reduced the toxic effect of acetochlor on maize or had any effect on the similar effect of antidote (N-dichloroacetyl-1-oxa-4-aza-spirodecane).

Effect of the active ingredients on the height of maize in % of the control

| No. of treatments according to Example (5b) | Alteration in height in maize culture on the | | |
|---|---|---|---|
| | 15th | 30th day | 45th |
| 1 | 100 | 100 | 100 |
| 2 | 56 | 87 | 100 |
| 3 | 124 | 115 | 103 |
| 4 | 109 | 103 | 101 |
| 5 | 116 | 109 | 105 |
| 6 | 92 | 101 | 100 |

The results show that the compounds according to the invention counterbalance the toxicity of acetochlor and increase the efficiency of the antidote tested.

EXAMPLE 5c

2'-Methyl-6'-ethyl-N-ethoxymethyl-chloroacetanilide (acetochlor), 2-chloro-N-isopropylacetanilide (propachlor) and 2-chloro-2',6'-diethyl-N-(methoxymethyl)-acetanilide as typical representatives of chloroacetanilide herbicides were combined with the compound according to Example 3 and a herbicidally active urea derivative, chlorobromuron (3-(4-bromo-3-chlorophenyl)-1-methoxy-1-methyl-urea).

The test conditions were identical with those described in Example 5, except that in addition to monocotyledonous weeds also dicotyledons (Amaranthus retroflexus) were sown.

The following treatments were carried out:
(1) control
(2) 2'-methyl6'-ethyl-N-ethoxymethyl-chloroacetanilide 2 kg/ha
(3) 2-chloro-N-isopropylacetanilide 4 kg/ha
(4) 2-chloro-2',6'-diethyl-N-(methoxymethyl)-acetanilide 2,5 kg/ha
(5) 3-(4-bromo-3-chlorophenyl)-1-methoxy-1-methyl-urea 1.5 kg/ha
(6) compound according to Example 3 1.0 kg/ha
(7) 2'-methyl-6'-ethyl-N-ethoxymethyl-chloroacetanilide 2.0 kg/ha+3-(3-bromo-3-chlorophenyl)-1-methoxy-1-methyl-urea 1.5 kg/ha+compound according to Example 3 1.0 kg/ha
(8) 2-chloro-N-isopropylacetanilide 4 kg/ha+3-(4-bromo-3-chlorophenyl)-1-methoxy-1-methyl-urea 1.5 kg/ha+compound according to Example 3 1.0 kg/ha
(9) 2-chloro-2',6'-diethyl-N-(methoxymethyl)acetanilide 2.5 kg/ha+compound according to Example 3 1.0 kg/ha
(10) compound according to Example 3 0.4 kg/ha
(11) 2'-methyl-6'-ethyl-N-ethoxymethyl-chloroacetanilide 2.0 kg/ha+3-(4-bromo-3-chlorophenyl)-1-methoxy-1-methyl-urea 1.5 kg/ha+compound according to Example 3 0.4 kg/ha
(12) 2-chloro-N-isopropylacetanilide 4.0 kg/ha+3-(4-bromo-3-chlorophenyl)-1-methoxy-1-methyl-urea 1.5 kg/ha+compound according to Example 3 0.4 kg/ha
(13) 2-chloro-2',6'-diethyl-N-(methoxymethyl)acetanilide 2.5 kg/ha+compound according to Example 3 0.4 kg/ha The effect of the active ingredients on the killing rate of wild millet (Panicum ssp) and amaranth (Amaranthus ssp).

| No. of treatments according to Example (5c) | Killing in % of the control on the |||||| 
|---|---|---|---|---|---|---|
| | 15th || 30th day || 45th ||
| | W.M. | A.R. | W.M. | A.R | W.M. | A.R. |
| 1 | 0 | 0 | 0 | 0 | 0 | 0 |
| 2 | 26 | 67 | 0 | 37 | 0 | 0 |
| 3 | 0 | 51 | 0 | 19 | 0 | 0 |
| 4 | 15 | 60 | 0 | 23 | 0 | 0 |
| 5 | 0 | 82 | 0 | 19 | 0 | 0 |
| 6 | 11 | 0 | 0 | 0 | 0 | 0 |
| 7 | 100 | 100 | 100 | 81 | 62 | 58 |
| 8 | 76 | 100 | 57 | 83 | 41 | 54 |
| 9 | 83 | 100 | 61 | 78 | 50 | 51 |
| 10 | 0 | 0 | 0 | 0 | 0 | 0 |
| 11 | 92 | 100 | 75 | 78 | 54 | 53 |
| 12 | 59 | 100 | 43 | 81 | 29 | 60 |
| 13 | 77 | 100 | 56 | 74 | 37 | 62 |

W.M. = wild millet
A.R. = amaranth

From the results it can be concluded that the compounds according to the invention improve the duration and extent of activity of chloroacetanilide herbicides also in combination with herbicidally active urea derivatives.

EXAMPLE 5d

Under similar conditions to those described in Example 5 we examined the herbicidal activity of combinations of herbicidally active chloroacetanilides and triazines in association with the compound according to Example 1. As weeds wild millet (Panicum ssp) and amaranth (Amaranthus ssp) were employed.

The following treatments were carried out:
(1) control
(2) 2'-methyl-6'-ethyl-N-ethoxymethyl-chloroacetanilide 2.0 kg/ha
(3) 2-chloro-4-ethylamino-6-isopropylamino-1,3,4-triazine 1.0 kg/ha
(4) 2-ethylamino-4-isopropylamino-6-methylthio-1,3,5-triazine 1.0 kg/ha
(5) 2,4-bis(isopropylamino)-6-methoxy-1,3,5-triazine 1.0 kg/ha
(6) 2-(4-chloro-6-ethylamino-1,3,5-triazine-2-yl-amino)-2-methyl-propionitrile 1.0 kg/ha
(7) compound according to Example 1 1.0 kg/ha
(8) compound according to example 1 0.4 kg/ha
(9) 2'-methyl-6'-ethyl-N-ethoxymethyl-chloroacetanilide 2.0 kg/ha+2-chloro-4-ethylamino-6-isopropylamino-1,3,5-triazine 1.0 kg/ha+compound according to Example 1 1.0 kg/ha
(10) 2'-methyl-6'-ethyl-N-ethoxymethyl-chloroacetanilide 2.0 kg/ha+2-chloro-4-ethylamino-6-isopropylamino-1,3,5-triazine 1.0 kg/ha+compound according to Example 1 0.4 kg/ha
(11) 2'-methyl-6'-ethyl-N-ethoxymethyl-chloroacetanilide 2.0 kg/ha+2-ethylamino-4-isopropylamino-6-methylthio-1,3,5-triazine 1.0 kg/ha+compound according to Example 1 1.0 kg/ha
(12) 2'-methyl-6'-ethyl-N-ethoxymethyl-chloroacetanilide 2.0 kg/ha+2-ethylamino-4-isopropylamino-6-methylthio-1,3,5-triazine 1.0 kg/ha+compound according to Example 1 0.4 kg/ha
(13) 2'-methyl-6'-ethyl-N-ethoxymethyl-chloroacetanilide 2.0 kg/ha+2,4-bis(isopropylamino)-6-methoxy-1,3,5-triazine 1.0 kg/ha+compound according to Example 1 1.0 kg/ha
(14) 2'-methyl-6'-ethyl-N-ethoxymethyl-chloroacetanilide 2.0 kg/ha+2,4-bis(isopropylamino)-6-methoxy-1,3,5-triazine 1.0 kg/ha+compound according to Example 1 0.4 kg/ha
(15) 2'-methyl-6'-ethyl-N-ethoxymethyl-chloroacetanilide 2.0 kg/ha+2-(4-chloro-6-ethylamino-1,3,5-triazine-2-ylamino)-2-methyl-propionitrile 1.0 kg/ha+compound according to Example 1 1.0 kg/ha
(16) 2'-methyl-6'-ethyl-N-ethoxymethyl-chloroacetanilide 2.0 kg/ha+2-(4-chloro-6-ethylamino-1,3,5-triazine-2-ylamino)-2-methyl-propionitrile 1.0 kg/ha+compound according to Example 1 0.4 kg/ha

| The effect of the active ingredients on killing rate (%) of wild millet (Panicum ssp) and amaranth (Amaranthus ssp) ||||||| 
|---|---|---|---|---|---|---|
| No. of treatments according to Example (5 d) | Killing ratio (%) related to the control on the ||||||
| | 15th || 30th day || 45th ||
| | W.M. | A.R. | W.M. | A.R. | W.M. | A.R. |
| 1 | 0 | 0 | 0 | 0 | 0 | 0 |
| 2 | 26 | 67 | 0 | 37 | 0 | 0 |
| 3 | 14 | 92 | 6 | 61 | 0 | 48 |
| 4 | 19 | 94 | 4 | 70 | 0 | 53 |
| 5 | 20 | 89 | 11 | 66 | 0 | 44 |
| 6 | 16 | 98 | 7 | 72 | 0 | 56 |
| 7 | 11 | 0 | 0 | 0 | 0 | 0 |
| 8 | 0 | 0 | 0 | 0 | 0 | 0 |
| 9 | 100 | 100 | 100 | 100 | 66 | 87 |
| 10 | 100 | 100 | 87 | 100 | 59 | 74 |
| 11 | 100 | 100 | 100 | 100 | 61 | 81 |
| 12 | 100 | 100 | 80 | 95 | 54 | 70 |
| 13 | 100 | 100 | 100 | 100 | 52 | 77 |
| 14 | 100 | 100 | 79 | 92 | 46 | 70 |
| 15 | 100 | 100 | 95 | 100 | 62 | 79 |
| 16 | 100 | 100 | 76 | 96 | 57 | 71 |

W.M. = wild millet
A.R. = amaranth

As the results set forth in the Table above the compound according to Example 1 increased the activity and extended the duration of activity of combinations containing chloroacetanilides (2'-methyl-6'-ethyl-N-ethoxymethyl-chloroacetanilide) and various triazines in the usual doses and mutual proportions.

EXAMPLE 6

In this experiment the effect of the compound according to the invention on the duration of activity of thiolcarbamate herbicides and on their combinations with antidotes was tested.

Tests were carried out as described in Example 5, except that, as usual in case of thiolcarbamate herbicides, the compositions were admixed with the soil prior to sowing.

The following treatments were carried out:
(1) control
(2) S-ethyl-dipropylthiolcarbamate (EPTC) 5 kg/ha
(3) S-ethyl-dipropylthiolcarbamate (EPTC) 5 kg/ha+N-dichloroacetyl-1-oxa-4-azaspiro-4,5-decane 350 g/ha (AD-67)
(4) S-ethyl-dipropylthiocarbamate (EPTC) 5 kg/ha+O,S-di-2-chloroethyl-S-(di-2-propenylamino)-dithiophosphoric acid ester 500 g/h (compound according to Example 2)
(5) S-ethyl-dipropylthiocarbamate (EPTC) 5 kg/ha+N-dichloroacetyl-1-oxa-4-azaspiro-4,5-dicane 350 g/ha (AD-67)+O,S-di-2-chloroethyl-S-(di-2-propenylamino)-dithiophosphoric acid ester 600 g/ha (compound according to Example 2)
(6) N-dichloroacetyl-1-oxa-4-azaspiro-4,5-decane 350 g/ha (AD-67)+O,S-2-chloroethyl-S-(di-2- propenylamino)-dithiophosphoric acid ester 500 g/ha (compound according to Example 2)
(7) N-dichloroacetyl-1-oxa-4-azaspiro-4,5-decane 450 g/ha (AD-67)
(8) O,S-di-2-chloroethyl-S-(di-propenylamino)-dithiophosphoric acid ester 500 g/ha (compound according to Example 2)

The effect of active ingredients on the killing rate (%) of wild millet (Panicum ssp)

| No. of treatments according to Example 6 | Killing rate in %-age of the control on the | | |
|---|---|---|---|
| | 15th | 30th day | 45th |
| 1 | 0 | 0 | 0 |
| 2 | 100 | 0 | 0 |
| 3 | 100 | 0 | 0 |
| 4 | 100 | 100 | 90 |
| 5 | 100 | 97 | 80 |
| 6 | 0 | 0 | 0 |
| 7 | 0 | 0 | 0 |
| 8 | 0 | 0 | 0 |

The effect of active ingredients on the extent of injury of maize (Zea mays)-phytotoxicity

| No. of treatments according to Example 6 | Alteration in height in %-age of the control | | |
|---|---|---|---|
| | 15th | 30th day | 45th |
| 1 | 100 | 100 | 100 |
| 2 | 69 | 100 | 100 |
| 3 | 82 | 100 | 100 |
| 4 | 94 | 100 | 100 |
| 5 | 121 | 110 | 106 |
| 6 | 134 | 118 | 111 |
| 7 | 102 | 100 | 100 |
| 8 | 129 | 120 | 108 |

The results show that under the provocative conditions described in Example 5 the test compound of formula (I) extended the duration of activity of S-ethyl-dipropyl-thiolcarbamate to three-fold of the activity observed when the herbicide was used either alone or in combination with the given antidote in the usual doses.

It can be concluded, too, that the compound according to Example 2, selected as a representative of the compounds of formula (I), has no effect on the test weed when employed alone, in the given dose. It is highly surprising that the compound according to Example 2 substantially extends the active period of thiolcarbamate herbicides even under provocative conditions (acceleration of decomposition).

Evaluation of the phytotoxicity studies shows that the test compound according to the invention reduces the undesired effect of thiolcarbamate herbicides on the cultivated plant testes (maize). The same effect was observed when the combinations were antidoted. It can further be concluded that compounds of formula (I) are not phytotoxic themselves.

The antidotal activity of the compounds according to the invention as well as their effect on the efficiency of a known antidote were tested by measuring the height of maize treated, and calculating the change related to the control.

It can be seen that EPTC when used without any antidote decreased the height of maize by 31% according to the evaluation performed on the 15th day. In case of antidoted EPTC combinations the reduction in height was 18% only. In case of later sowings (evaluations carried out on the 30th and 45th days, respectively) there was no change in height. The combination of EPTC with the compound according to Example 2 resulted in a further reduction of the decrease in height: the decrease was only 6% according to the evaluation performed on the 15th day.

When the antidoted EPTC formulation and the active ingredient according to the invention were sprayed together on maize (treatment No. 5), the height of the maize exceeded the height of the control. Combined application of the test antidote and the active ingredient according to the invention resulted in a further increase in the growth of maize. From the results it can be concluded that the compounds according to the invention increase the efficiency of antidotes of herbicidally active thiolcarbamates (N-dichloroacetyl-1-oxa-azaspiro-4,5-decane; N,N-diallyl-2,2-dichloroacetamide; 3-(dichloroacetyl)-2,2-dimethyl-1,3-oxazolidine).

The results discusses in Example 6 unambiguously prove that the active ingredients according to the invention on the one hand increase the activity of herbicidally active thiolcarbamates and extend the duration of their activity, on the other hand, improve the selectivity of said herbicides and their combinations with antidotes and extend the period within which said formulations can be used safely.

EXAMPLE 6a

In this example the herbicidal activity, and the effective doses of herbicidally active thiolcarbamates alone and in combination of compounds according to the invention were examined.

The test conditions were identical with those described in Examples 5 and 6, except that the herbicidal activity and the duration of activity were examined.

The following treatments were carried out:
(1) control
(2) butylate (S-ethyl-diisobutyl(thiolcarbamate)) 4.0 kg/ha
(3) butylate 3 kg/ha
(4) cycloate (S-ethyl-N-cyclohexyl-N-ethyl(thiolcarbamate)) 4 kg/ha
(5) cycloate 2 kg/ha
(6) vernolate (S-propyl-dipropyl(thiolcarbamate)) 4 kg/ha
(7) vernolate 3 kg/ha
(8) butylate 4 kg/ha+compound according to Example 3 1 kg/ha
(9) butylate 3 kg/ha+compound according to Example 3 0.75 kg/ha
(10) cycloate 4 kg/ha+compound according to Example 3 1 kg/ha
(11) cycloate 3 kg/ha+compound according to Example 3 0.75 kg/ha
(12) vernolate 4 kg/ha+compound according to Example 3 1 kg/ha
(13) vernolate 3 kg/ha+compound according to Example 3 0.75 kg/ha
(14) compound according to Example 3 1 kg/ha
(15) compound according to Example 3 0.75 kg/ha The compositions were thoroughly admixed with the soil prior to sowing.

The effect of the active ingredients on the killing ratio (%) of wild millet (Panicum ssp)

| No. of treatments according to Example (6a) | Killing rate in %-age of control on the | | |
|---|---|---|---|
| | 15th | 30th day | 45th |
| 1 | 0 | 0 | 0 |
| 2 | 100 | 11 | 0 |
| 3 | 75 | 0 | 0 |
| 4 | 10 | 7 | 0 |
| 5 | 63 | 0 | 0 |
| 6 | 100 | 0 | 0 |
| 7 | 66 | 0 | 0 |
| 8 | 100 | 100 | 86 |
| 9 | 100 | 77 | 52 |
| 10 | 100 | 100 | 81 |
| 11 | 100 | 80 | 60 |
| 12 | 100 | 100 | 54 |
| 13 | 100 | 83 | 59 |
| 14 | 0 | 0 | 0 |
| 15 | 0 | 0 | 0 |

The test results show that the duration of the activity of herbicidally active thiolcarbamates can be expanded and their dose can be reduced, if they are combined with the active ingredients according to the invention.

EXAMPLE 6b

The increase in the duration of herbicidal activity and the decrease of their effective dose were tested in case of thiolcarbamate herbicides, which need not be admixed with the soil prior to sowing in order to achieve the desired effect.

The test conditions were as described in Example 6.
(1) control
(2) diallate (S-2,3-dichloroallyl-diisopropyl(thiolcarbamate)) 1.2 kg/ha
(3) diallate 0.6 kg/ha
(4) triallate (S-2,3,3-trichloroallyl-diisopropyl(thiolcarbamate)) 2.0 kg/ha
(5) triallate 1.0 kg/ha
(6) pebulate (S-propyl-butyl(ethyl)thiolcarbamate) 3.0 kg/ha
(7) pebulate 1.5 kg/ha
(8) molynate (S-ethyl-N,N-hexamethylenethiolcarbamate) 3.0 kg/ha
(9) molynate 1.5 kg/ha
(10) sulfallate (2-chloroallyl-diethyl-dithiocarbamate) 4.0 kg/ha
(11) sulfallate 2.0 kg/ha
(12) diallate 1.2 kg/ha+compound No. 1 0.25 kg/ha
(13) diallate 0.6 kg/ha+compound No. 1 0.125 kg/ha
(14) triallate 2 kg/ha+compound No. 1 0.4 kg/ha
(15) triallate 1 kg/ha+compound No. 1 0.2 kg/ha
(16) pebulate 3 kg/ha+compound No. 1 0.5 kg/ha
(17) pebulate 1.5 kg/ha+compound No. 1 0.25 kg/ha
(18) molynate 3 kg/ha+compound No. 1 0.5 kg/ha
(19) molynate 1.5 kg/ha+compound No. 1 0.25 kg/ha
(20) sulfallate 4 kg/ha+compound No. 1 0.8 kg/ha
(21) sulfallate 2 kg/ha+compound No. 1 0.4 kg/ha Unlike in the previous tests instead of wild millet (Panicum ssp) wild oat (Avena fatua) was used as a test plant, since the above-mentioned herbicides are particularly effective against wild oat, though they are active also against other monocotyledonous weeds.

The effect of the compounds according to the invention on the killing rate (%) of wild oat (Avena fatua)

| No. of treatments according to Example (6b) | Killing rate in %-age of the control on the | | |
|---|---|---|---|
| | 15th | 30th day | 45th |
| 1 | 0 | 0 | 0 |
| 2 | 79 | 0 | 0 |
| 3 | 31 | 0 | 0 |
| 4 | 83 | 5 | 0 |
| 5 | 42 | 0 | 0 |
| 6 | 67 | 0 | 0 |
| 7 | 22 | 0 | 0 |
| 8 | 71 | 0 | 0 |
| 9 | 26 | 0 | 0 |
| 10 | 88 | 11 | 0 |
| 11 | 41 | 0 | 0 |
| 12 | 100 | 100 | 69 |
| 13 | 100 | 69 | 51 |
| 14 | 100 | 100 | 100 |
| 15 | 100 | 89 | 66 |
| 16 | 100 | 100 | 92 |
| 17 | 100 | 81 | 59 |
| 18 | 100 | 100 | 71 |
| 19 | 100 | 76 | 61 |
| 20 | 100 | 100 | 100 |
| 21 | 100 | 84 | 75 |

Examination of the thiolcarbamate herbicides shows that they are ineffective two weeks after the treatment. If, however, they are combined with compound No. 1 according to the invention, their activity lasts more than two-times as long as originally. In addition, their activity is also increased. Decreasing the dose of the thiolcarbamate herbicides tested but combining them with the compound No. 1, the death of wild oat is 100% at the first evaluation even if the dose of the herbicide is decreased to half of its original amount.

A more than 50% death is observed even during the third evaluation (45th day) when a combination was employed, while the herbicides alone, even in the complete original doses, were ineffective (0%) 45 days after treatment.

EXAMPLE 6c

The test conditions were the same as in Examples 5 and 6, except that in addition to wild millet (Panicum ssp) amaranth (Amaranthus ssp) was used as a test weed.

The following treatments were carried out:
(1) control
(2) S-ethyl-dipropylcarbamothioate 5.0 kg/ha+N-dichloroacetyl-1-oxy-4-azaspiro-4,5-decane 5.5 kg/ha
(3) S-ethyl-diisobutylthiocarbamate 5.0 kg/ha+N,N-diallyl-2,2-dichloroacetamide 0.5 kg/ha
(4) 2-chloro-4-ethylamino-6-isopropylamino-1,3,5-triazine 1.5 kg/ha
(5) 2-chloro-4-ethylamino-6-isopropylamino-1,3,5-triazine 0.75 kg/ha
(6) 2-(4-chloro-6-ethylamino-1,3,5-triazine-2-ylamino)-2-methylpropyonitrile 1.5 kg/ha
(7) 2-(4-chloro-6-ethylamino-1,3,5-triazine-2-ylamino)-2-methylpropionitrile 0.75 kg/ha
(8) compound according to Example 3 1.0 kg/ha
(9) S-ethyl-dipropylcarbamothioate 5.0 kg/ha+N-dichloroacetyl-1-oxa-4-azaspiro-4,5-decane 0.5 kg/ha+2-chloro-4-ethylamino-6-isopropylamino-1,3,5-triazine 1.5 kg/ha+compound according to Example 3 1.0 kg/ha

(10) S-ethyl-dipropylcarbamothioate 5.0 kg/ha+N-dichloroacetyl-1-oxa-4-azaspiro-4,5-decane 0.5 kg/ha+2-chloro-4-ethylamino-6-isopropylamino-1,3,5-triazine 0.75 kg/ha+compound according to Example 3 1.0 kg/ha
(11) S-ethyl-dipropylcarbamothioate 5.0 kg/ha+N-dichloroacetyl-1-oxa-4-azaspiro-4,5-decane 0.5 kg/ha+2-(4-chloro-6-ethylamino-1,3,5-triazine-2-yl-amino)-2-methyl-propionitrile 1.5 kg/ha+compound according to Example 3 1.0 kg/ha
(12) S-ethyl-dipropylcarbamothioate 5.0 kg/ha+N-dichloroacetyl-1-oxa-4-azaspiro-4,5-decane 0.5 kg/ha+2-(4-chloro-6-ethylamino-1,3,5-triazine-2-ylamino)-2-methyl-propionitrile 0.75 kg/ha+compound according to Example 3 1.0 kg/ha
(13) S-ethyl-diisobutyl-thiocarbamate 5.0 kg/ha+N,N-diallyl-1,2-dichloroacetamide 0.5 kg/ha+2-chloro-4-ethylamino-6-isopropylamino-1,3,5-triazine 1.5 kg/ha+compound according to Example 3 1.0 kg/ha
(14) S-ethyl-diisobutyl-thiolcarbamate 5.0 kg/ha+N,N-diallyl-2,2-dichloroacetamide 0.5 kg/ha+2-chloro-4-ethylamino-6-isopropylamino-1,3,5-triazine 0.75 kg/ha+compound according to Example 3 1.0 kg/ha
(15) S-ethyl-diisobutyl-thiolcarbamate 5.0 kg/ha+N,N-diallyl-2,2-dichloroacetamide 0.5 kg/ha+2-(4-chloro-6-ethylamino-1,3,5-triazine-2-yl-amino)-2-methylpropionitrile 1.5 kg/ha+compound according to Example 3 1.0 kg/ha
(16) S-ethyl-diisobutyl-thiolcarbamate 5.0 kg/ha+N,N-diallyl-2,2-dichloroacetamide 0.5 kg/ha+2-(4-chloro-6-ethylamino-1,3,5-triazine-2-yl-amino)-2-methylpropionitrile 0.75 kg/ha+compound according to Example 3 1.0 kg/ha

| No. of treatments according to Example (6c) | Killing rate in % age of the control on the | | | | | |
|---|---|---|---|---|---|---|
| | 15th | | 30th day | | 45th | |
| | W.M. | A.R. | W.M. | A.R. | W.M. | A.R. |
| 1 | 0 | 0 | 0 | 0 | 0 | 0 |
| 2 | 100 | 67 | 0 | 0 | 0 | 0 |
| 3 | 100 | 59 | 0 | 0 | 0 | 0 |
| 4 | 34 | 93 | 11 | 60 | 0 | 31 |
| 5 | 11 | 49 | 0 | 21 | 0 | 0 |
| 6 | 38 | 90 | 13 | 64 | 0 | 25 |
| 7 | 14 | 42 | 0 | 25 | 0 | 0 |
| 8 | 0 | 0 | 0 | 0 | 0 | 0 |
| 9 | 100 | 100 | 100 | 100 | 69 | 78 |
| 10 | 100 | 100 | 100 | 100 | 57 | 71 |
| 11 | 100 | 100 | 100 | 100 | 72 | 76 |
| 12 | 100 | 100 | 100 | 100 | 51 | 69 |
| 13 | 100 | 100 | 100 | 100 | 71 | 74 |
| 14 | 100 | 100 | 100 | 100 | 56 | 67 |
| 15 | 100 | 100 | 100 | 100 | 67 | 70 |
| 16 | 100 | 100 | 100 | 100 | 41 | 56 |

Thiolcarbamate herbicides are often combined with herbicidally active triazine derivatives, to widen their activity spectrum.

Examination of the activity of the combinations containing herbicidally active thiolcarbamates, triazines and compounds according to the invention shows that the compound according to the invention extend the duration of activity and increase the activity of the test combinations. Accordingly, compounds of the formula (I) excert their favourable effects not only in combination with thiolcarbamate herbicides alone but also if they are combined with various herbicidally active triazine derivatives.

EXAMPLE 7

The effect of the compounds according to the invention on the duration and extent of herbicidal activity of various herbicidally active thiolcarbamates were examined.

The test were carried out essentially as described in Example 6, except that as a cultivated plant 5 pieces of soya were cultivated in each pot.

The following treatments were performed:
(1) control
(2) 1-methylethyl-3-chlorophenyl-carbamate 2 kg/ha
(3) 1-methylethyl-3-chlorophenyl-carbamate 1 kg/ha
(4) 1-methylethyl-3-chlorophenyl-carbamate 2 kg/ha+compound according to Example 3 0.5 kg/ha
(5) 1-methylethyl-3-chlorophenyl-carbamate 1 kg/ha+compound according to Example 3 0.5 kg/ha
(6) 1-methylethyl-3-chlorophenyl-carbamate 2 kg/ha+compound according to Example 1 0.25 kg/ha
(7) 1-methylethyl-3-chlorophenyl-carbamate 1 kg/ha+compound according to Example 1 0.25 kg/ha

| The effect of active ingredients on the killing rate (%) of wild millet (Panicum ssp) | | | |
|---|---|---|---|
| No. of treatments according to Example 7 | Killing rate in % age of the control on the | | |
| | 15th | 30th day | 45th |
| 1 | 0 | 0 | 0 |
| 2 | 23 | 0 | 0 |
| 3 | 8 | 00 | 0 |
| 4 | 95 | 64 | 40 |
| 5 | 74 | 53 | 29 |
| 6 | 97 | 73 | 55 |
| 7 | 66 | 41 | 30 |

The results set forth in the above Table show that 1-methylethyl-3-chlorophenyl-carbamate alone is practically ineffective against wild oat in the test doses. The addition of the compound according to Example 1 has considerably increased the herbicidal activity in each combination tested, and the combinations which contained the compounds according to the invention were considerably more effective even on the 45th day after treatment than those containing the above-mentioned carbamate derivative as a sole active ingredient on the 15th day.

The effect of the above combinations on cultivated plants was tested on soya. Injury rating was carried out on the basis of EWRC scale. 1 means that there was no injury observed, 9 stands for total killing.

| Phytotoxicity on soya using the combinations according to the invention | | | |
|---|---|---|---|
| No. of treatments according to Example 7 | Phytotoxicity (EWRC) on the | | |
| | 15th | 30th day | 45th |
| 1 | 1 | 1 | 1 |
| 2 | 2 | 1 | 1 |
| 3 | 1 | 1 | 1 |
| 4 | 2 | 1 | 1 |
| 5 | 1 | 1 | 1 |
| 6 | 1 | 1 | 1 |
| 7 | 1 | 1 | 1 |

It can be seen that the combination of 1-methylethyl-3-chlorophenyl-carbamate with the compound according to the invention resulted in no increase in phytotoxicity.

EXAMPLE 8

The effect of the combinations of thiolcarbamate and chloroacetanilides with compounds of formula (I) was examined.

Though they are generally applied to the fields differently (thiolcarbamates are to be incorporated into the soil while acetochlor should be sprayed on the surface), a common feature of thiolcarbamates and acetochlor is that both should be antidoted to avoid the undesired injury of cultivated plants (e.g. maize).

Tests were carried out in pot having a diameter of 12 cm filled with meadow chernosiom soil, in 6 repetitions. The corns of maize (5 pieces into each pot) were placed ia a depth of 8 cm measured from the top of the pots. Corns were then covered with a 5 to 6 cm thick soil layer admixed with the seeds of various weeds (cocksfoots weed, amaranth). Weeds were admixed with the soil in separate pots, each with 1 cm³ of soil. The combinations tested were then sprayed on the pots as a tank mixture, in an amount of 220 lit./ha. After spraying, the soil was covered with a 2 to 3 cm thick fresh soil layer, and the water capacity of the soil was adjusted to 65 to 70%.

On the 20th day after treatment the degree of weed control and the injury of cultivated plants were examined. On the 20th day the test plants were eliminated, and new weed seeds were admixed with the upper 3 to 5 thick layer of soil. The degree of weed control was examined and the efficiency of weed control was examined on the 40th day.

The following treatments were carried out:
(1) control
(2) S-ethyldiisobutylthiolarbamate 3 kg/ha+N,N-diallyl-2,2-dichloroacetamide 500 g/ha+2-chloro-2-methyl-6-ethyl-N-methoxyethylacetanilide 1.0 kg/ha
(3) S-ethyl-diisobutylthiolarbamate 2 kg/ha+N,N-diallyl-2,2-dichloroacetamide 500 g/ha+2-chloro-2-methyl-6-ethyl-N-methoxyacetanilide 2.0 kg/ha
(4) S-ethyl-dipropylcarbamothioate 4 kg/ha+N-dichloroacetyl-1-oxa-4-azaspiro-4,5-decane 800 g/ha+2-chloro-2-methyl-6-ethyl-N-methoxyacetanilide 1.5 kg/ha
(5) S-ethyl-dipropylcarbamothioate 3.5 kg/ha+N-dichloroacetyl-1-oxa-4-azaspiro-4,5-decane 800 g/ha+2-chloro-2-methyl-6-ethyl-N-methoxyacetanilide 2.0 kg/ha
(6) S-propyl-dipropylcarbamothioate 2.5 kg/ha+N-dichloroacetyl-1-oxa-spiro-4,5-decane 520 g/ha+2-chloro-2-methyl-6-ethyl-N-methoxyacetanilide 1.0 kg/ha
(7) S-propyl-dipropylcarbamothioate 1.5 kg/ha+N-dichloroacetyl-1-oxa-4-azaspiro-4,5-decane 520 g/ha+2-chloro-2-methyl-6-ethyl-N-methoxyacetanilide 2.0 kg/ha
(8) treatment No. 2+O,S-di-2-chloroethyl-S-(di-2-propenylamino)-dithiophosphoric acid ester (compound according to Example 2) 0.8 kg/ha
(9) treatment No. 3+O,S-di-2-chloroethyl-S-(di-2-propenylamino)-dithiophosphoric acid ester (compound according to Example 2) 0.8 kg/ha
(10) treatment No. 4+O,S-di-2-chloroethyl-S-(di-2-propenylamino)-dithiophosphoric acid ester (compound according to Example 2) 1 kg/ha
(11) treatment No. 5+O,S-di-2-chloroethyl-S-(di-2-propenylamino)-dithiophosphoric acid ester (compound according to Example 2) 1 kg/ha
(12) treatment No. 6+O,S-di-2-chloroethyl-S-(di-2-propenylamino)-dithiophosphoric acid ester (compound according to Example 2) 0.7 kg/ha
(13) treatment No. 7+O,S-di-2-chloroethyl-S-(di-2-propenylamino)-dithiophosphoric acid ester (compound according to Example 2) 0.7 kg/ha The effect of combinations on the killing rate of cocksfoot weed (Echinochloa ssp) and amaranth (Amaranthus ssp)

| No. of treatments | Killing in %-age of the control on the | | | |
|---|---|---|---|---|
| | 20th | | 40th | |
| | day | | | |
| | Ec. | Am. | Ec. | Am. |
| 1 | 0 | 0 | 0 | 0 |
| 2 | 100 | 100 | 32 | 14 |
| 3 | 100 | 100 | 27 | 31 |
| 4 | 100 | 100 | 27 | 29 |
| 5 | 100 | 100 | 35 | 36 |
| 6 | 100 | 100 | 28 | 21 |
| 7 | 100 | 100 | 36 | 33 |
| 8 | 100 | 100 | 72 | 69 |
| 9 | 100 | 100 | 88 | 74 |
| 10 | 100 | 100 | 79 | 71 |
| 11 | 100 | 100 | 87 | 78 |
| 12 | 100 | 100 | 64 | 79 |
| 13 | 100 | 100 | 67 | 76 |

Ec = cocksfoot weed
Am = amaranth
The killing rate was examined on the basis of green weight.
Killing rate (%) = green weight in %-age of the control.

Effect of the combinations on the height of maize and the ratio of malformation

| No. of treatments | Height of plant in %-age of the control | Ratio of malformation |
|---|---|---|
| | | on the basis of the average of 6 × 5 plants |
| 1 | 100.0 | — |
| 2 | 94.5 | 1 |
| 3 | 86.6 | — |
| 4 | 90.5 | — |
| 5 | 93.8 | — |
| 6 | 86.3 | 2 |
| 7 | 89.7 | 1 |
| 8 | 95.7 | — |
| 9 | 93.6 | — |
| 10 | 94.5 | — |
| 11 | 96.9 | — |
| 12 | 91.7 | — |
| 13 | 93.2 | 1 |

Evaluation of the activity of antidoted combinations of various thiolcarbamates (butylate, EPTC, vernolate) and acetochlor shows that they have no substantial phytotoxic effect on maize, if they are incorporated into the soil not too deeply. In addition, these combinations show an excellent herbicidal activity according to the evaluation carried out on the 20th day. The results of the second evaluation show, however, that their herbicidal activity considerably decreases as a function of time. On the 40th day they can control only 14 to 36% of the weeds tested. On the other hand, when O,S-di-2-chloroethyl-S-(di-2-propenylamino)-dithiophosphoric acid ester according to the invention was added to the test combinations, they killed 64 to 88% of the weeds at the time of second evaluation, too. Moreover, the compound according to the invention did not increase the phytotoxicity of the test combinations.

We claim:

1. A composition for the extension and increase of the activity of herbicidal compositions containing as herbicidally active ingredient a thiolcarbamate together with an herbicidal extender compound selected from the group consisting of O,S-di-2-chloroethyl-S-(di-2-propenylamino)-dithiophosphoric acid ester and O,S-diethyl-S-(di-2-propenylamino)-dithiophosphoric acid ester.

2. The composition defined in claim 1 for the extension and increase of the activity of herbicidal compositions wherein the thiolcarbamate is selected from the group consisting of S-ethyl-diisobutylthiolcarbamate, S-ethyl-N-cyclochexyl-N-ethyl-(thiolcarbamate), S-propyl-dipropyl(thiolcarbamate), S-2,3-dichloroallyl-diisopropyl-(thiolcarbamate), S-ethyl-N,N-hexamethylenethiolcarbamate, S-propyl-butyl(ethyl)-thiolcarbamate, S-2,3,3-trichloroallyl-diisopropyl-(thiolcarbamate) and 2-chloroallyl-diethyl-dithiolcarbamate, together with the herbicidal extender compound selected from the group consisting of O,S-di-2-chloroethyl-S-(di-2-propenylamino)-dithiophosphoric acid ester and O,S-diethyl-S-(di-2-propenylamino)-dithiophosphoric acid ester.

3. A composition for the extension and increase of the activity of herbicidal compositions containing as herbicidally active ingredient a chloroacetanilide or dichloroacetanilide together with an herbicidal extender compound selected from the group consisting of O,S-di-2-chloroethyl-S-(di-2-propenylamino)-dithiophosphoric acid ester and O,S-diethyl-S-(di-2-propenylamino)-dithiophosphoric acid ester.

* * * * *